(12) United States Patent
Yazawa (10) Patent No.: US 12,156,695 B2
(45) Date of Patent: Dec. 3, 2024

(54) OPHTHALMIC DEVICE

(71) Applicant: NIKON CORPORATION, Tokyo (JP)

(72) Inventor: Hiroki Yazawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 781 days.

(21) Appl. No.: 17/057,278

(22) PCT Filed: May 23, 2019

(86) PCT No.: PCT/JP2019/020545
§ 371 (c)(1),
(2) Date: Nov. 20, 2020

(87) PCT Pub. No.: WO2019/225716
PCT Pub. Date: Nov. 28, 2019

(65) Prior Publication Data
US 2021/0307602 A1    Oct. 7, 2021

(30) Foreign Application Priority Data

May 23, 2018    (JP) ................................ 2018-099122

(51) Int. Cl.
*A61B 3/10*    (2006.01)
*A61B 3/00*    (2006.01)
*A61B 3/15*    (2006.01)

(52) U.S. Cl.
CPC ............ *A61B 3/102* (2013.01); *A61B 3/0008* (2013.01); *A61B 3/158* (2013.01)

(58) Field of Classification Search
CPC ........ A61B 3/102; A61B 3/0008; A61B 3/158

USPC .......................................... 351/205–206, 246
See application file for complete search history.

(56) References Cited

U.S. PATENT DOCUMENTS

| 5,521,657 A | * | 5/1996 | Klopotek | ............. | A61B 5/0095 |
| | | | | | 351/212 |
| 2015/0272433 A1 | * | 10/2015 | Wang | ................... | A61B 3/0075 |
| | | | | | 351/221 |

FOREIGN PATENT DOCUMENTS

| JP | 02295537 A | * | 12/1990 | ............. | A61B 3/117 |
| JP | H02-295537 A | | 12/1990 | | |
| JP | H05-192295 A | | 8/1993 | | |
| JP | 2013-076587 A | | 4/2013 | | |

OTHER PUBLICATIONS

JP Office Action issued in corresponding Japanese Patent Application No. 2021-138401 dated Oct. 11, 2022 (3 pages).

* cited by examiner

*Primary Examiner* — James R Greece
(74) *Attorney, Agent, or Firm* — FOLEY & LARDNER LLP

(57) ABSTRACT

A model eye is disposed on a reference light path of reference light in a reference optical system so as to reflect or scatter the reference light at a model retina in order to form an interference optical system used to obtain interference light from the reference light of the reference optical system and signal light illuminated onto an examined eye in a signal optical system.

10 Claims, 7 Drawing Sheets

OPHTHALMIC DEVICE

CROSS-REFERENCE TO RELATED APPLICATION

This application is a National Stage of International Application No. PCT/JP2019/020545, filed May 23, 2019, the disclosure of which is incorporated herein by reference in its entirety. Further, this application claims priority from Japanese Patent Application No. 2018-099122, filed May 23, 2018, the disclosure of which is incorporated herein by reference in its entirety.

TECHNICAL FIELD

The technology disclosed herein relates to an ophthalmic device.

BACKGROUND ART

Optical coherence tomography (hereafter referred to as OCT) is widely utilized in ophthalmic devices that image fundus tomographic images of an examined eye by causing interference between signal light and reference light. Such technology is described in Patent Document 1.

RELATED ART LITERATURE

Patent Literature

Patent Document 1: Japanese Patent Application Laid-Open (JP-A) No. 2013-76587

SUMMARY OF INVENTION

An ophthalmic device of a first aspect of technology disclosed herein includes an interference optical system configured to obtain interference light from a signal light illuminated onto an examined eye and a reference light, and a model eye disposed on a reference light path of the reference light and configured to reflect or scatter the reference light at a model retina formed on a concave face.

DESCRIPTION OF EMBODIMENTS

Detailed explanation follows regarding exemplary embodiments of the present invention, with reference to the drawings.

First Exemplary Embodiment

An example of a configuration of an ophthalmic device 110 will now be described with reference to FIG. 1.

Figure 1:
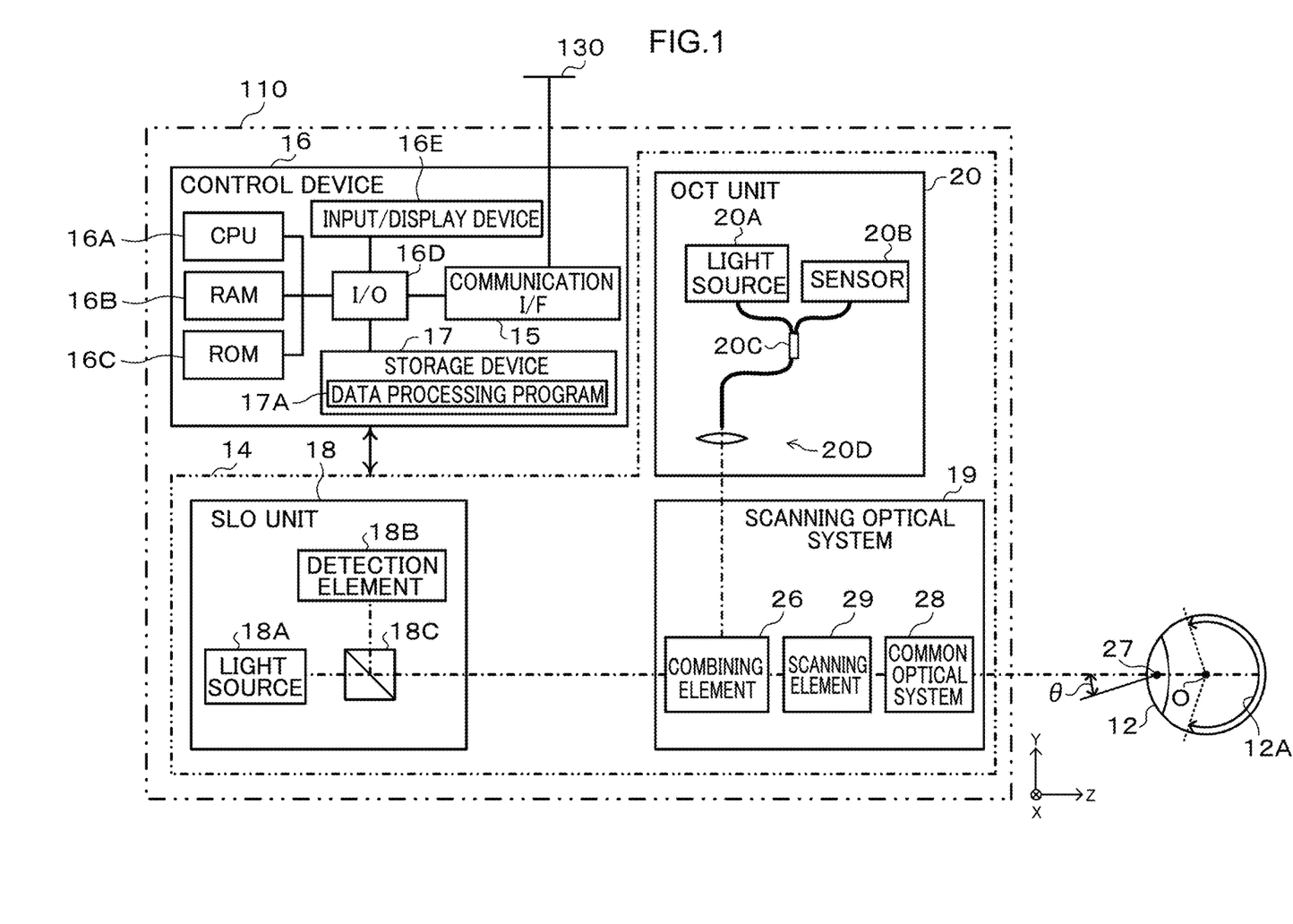
FIG. 1 is a configuration diagram illustrating an overall configuration of an ophthalmic device.

As illustrated in FIG. 1, the ophthalmic device 110 includes an imaging device 14 and a control device 16. The control device 16 is implemented by a computer including a central processing unit (CPU) 16A, random access memory (RAM) 16B, read only memory (ROM) 16C, and an input/output (I/O) port 16D. The ophthalmic device 110 is an example of an ophthalmic device of technology disclosed herein.

A data processing program 17A for controlling the ophthalmic device 110 is stored in a storage device 17. Note that although a case in which the data processing program 17A is stored in the storage device 17 will be described here, the technology disclosed herein is not limited thereto, and the data processing program 17A may be stored in the ROM 16C.

The storage device 17 is connected to the input/output (I/O) port 16D. Note that the storage device 17 may, for example, be configured from non-volatile memory (NVM). The input/output (I/O) port 16D is connected to a network 130 through a communication interface (I/F) 15.

The control device 16 includes an input/display device 16E connected through the I/O port 16D. The input/display device 16E includes a graphical user interface to display images obtained by imaging and to receive various instructions, including instructions relating to imaging. An example of such a graphical user interface is a touch panel display. Note that for ease of explanation "imaging" refers to a user using the ophthalmic device 110 to obtain an image representing an imaging subject.

The imaging device 14 is operated under control from the control device 16. The imaging device 14 includes a scanning laser ophthalmoscope (hereafter referred to as SLO) unit 18 for imaging (SLO imaging) of en-face images of a fundus, a scanning optical system 19, and an OCT unit 20 for imaging (OCT imaging) to obtain tomographic images of a retina and 3D OCT data of a fundus.

Note that the OCT installed in the ophthalmic device 110 may be either a spectral domain OCT (SD-OCT) or a swept source OCT (SS-OCT). Moreover, the OCT unit 20 and the scanning optical system 19 configured according to the technology disclosed herein may be combined as appropriate with a fundus imaging device such as a fundus camera, a slit lamp, an ophthalmic surgical microscope, or the like. Alternatively, the configuration according to the technology disclosed herein may be incorporated into a standalone OCT.

The SLO imaging is implemented by the control device 16, the SLO unit 18, and the scanning optical system 19. The SLO unit 18 includes a light source 18A, a detection element 18B, a beam splitter 18C, and the like. The light source 18A includes a red light (R light) light source, a green light (G light) light source, a blue light (B light) light source, and an infrared (for example, near-infrared) light source. The light source 18A is configured so as to be capable of switching between a mode in which emit R light and G light is emitted, a mode in which B light is emitted, and a mode in which infrared light is emitted. The scanning optical system 19 includes a combining element 26 configured from a dichroic mirror or the like, a scanning element 29 configured from a MEMS mirror or the like so as to perform two-dimensional scanning, and a common optical system 28.

Light from the SLO unit 18 (hereafter referred to as "SLO light") is scanned by the scanning element 29 in an X direction (horizontal direction) and a Y direction (vertical direction), and is made to pass through a pupil position Pp of an examined eye 12 by the scanning optical system 19 so as to be illuminated onto an imageable region 12A.

Reflected light or scattered light from the examined eye 12 passes through the scanning optical system 19 and the beam splitter 18C of the SLO unit to be picked up by the detection element 18B. A photoreception signal of the detection element 18B is processed by the control device 16 to obtain an en-face fundus image.

Explanation follows regarding the field of view (FOV) of the fundus imaged by the ophthalmic device 110. An imageable region 12A is a maximum region scannable by the scanning optical system 19. An example of the imageable region 12A is a range that provides a field of view for an external illumination angle of 140°. Such a case corresponds to an internal illumination angle of around 200°.

The external illumination angle refers to the incident angle of signal light with respect to the center of the pupil of the examined eye 12 (corresponding to the angle θ in FIG. 1). The internal illumination angle represents an angular range imaged by scanning the SLO light with respect to a reference position of a center O of the eyeball of the examined eye 12.

OCT imaging is implemented by the control device 16, the OCT unit 20, and the scanning optical system 19. The OCT unit 20 includes a light source 20A that emits a laser beam having a near infrared wavelength, a sensor 20B, and a fiber coupler 20C. Tomographic images of the retina and the choroid present in a Z direction region of the fundus or 3D OCT data of a fundus are obtained by OCT imaging. Since the scanning optical system mentioned above is also employed in the OCT imaging, imaging of the imageable region 12A is possible.

The light from the light source 20A of the OCT unit 20 (hereafter referred to as "OCT light") passes through the fiber coupler 20C, is collimated into a parallel beam by a collimator 20D, and is emitted toward the scanning optical system 19. The light source 20A employs a broad waveband super luminescent diode (SLD) light source or the like in the case of SD-OCT, and is a wavelength sweeping light source that sweeps wavelength at high speed in the case of SS-OCT.

The emitted OCT light is split into reference light and signal light by a half mirror 20E (see FIG. 2) within the scanning optical system 19. The signal light passes through a pupil of the examined eye 12 (pupil position Pp), and is scanned over the imageable region 12A in an X direction (horizontal direction) and a Y direction (vertical direction) by the scanning element 29. On the other hand, the reference light passes through a pupil of a model eye 21, described later, and is scanned over a model retina 218 in the X direction (horizontal direction) and the Y direction (vertical direction) by the scanning element 29. The signal light reflected or scattered by the retina and the choroid, and the reference light reflected or scattered by the model retina 218 of the model eye 21, are recombined by the half mirror 20E so as to interfere with each other. The resulting interference light then passes through the fiber coupler 20C and is incident to the sensor 20B where it is detected as an interference signal. The control device 16 employs the detection result of the sensor 20B to generate tomographic images and the like. The scanning optical system 19 and the OCT unit 20 are examples of an interference optical system of technology disclosed herein.

Figure 2:
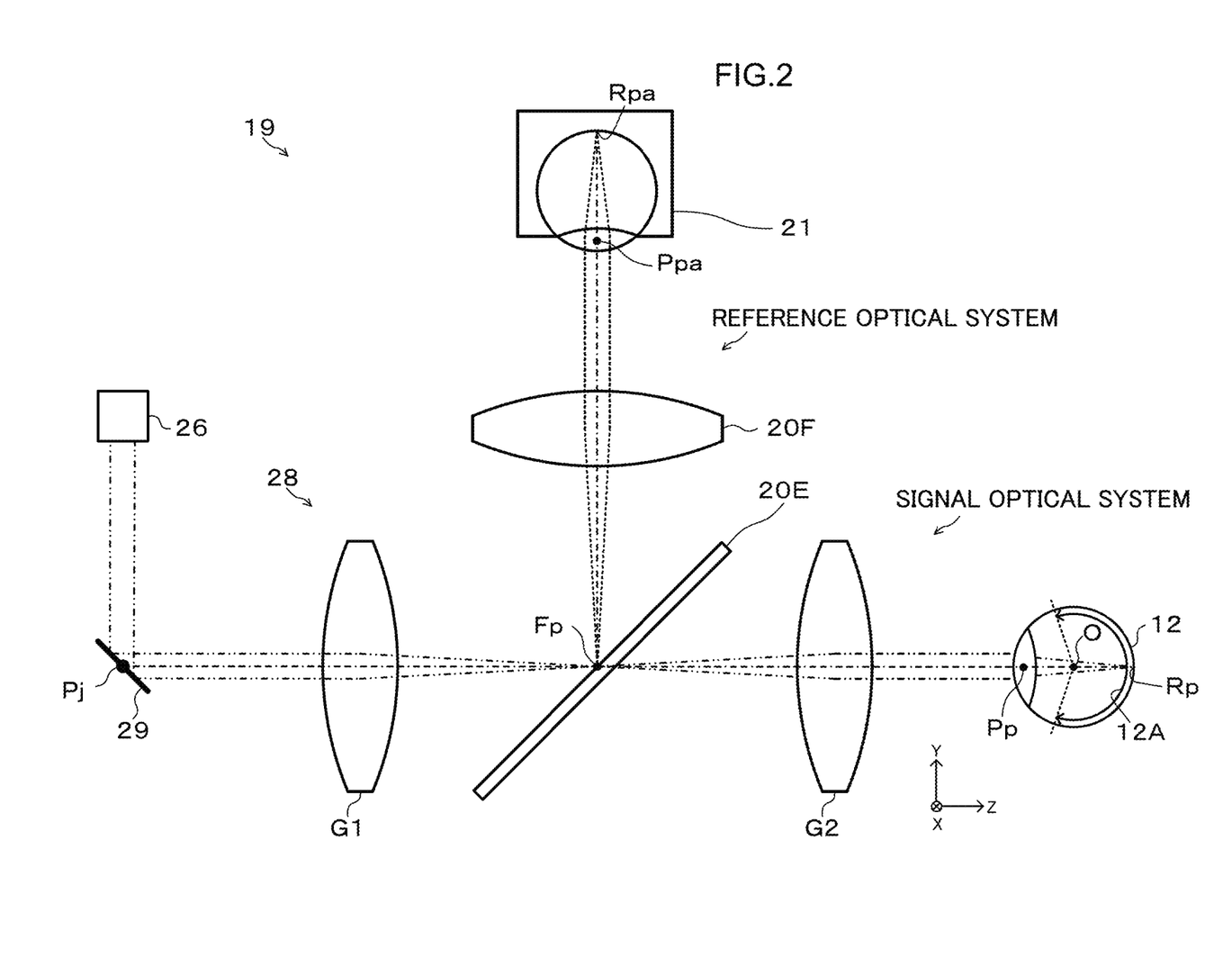
FIG. 2 is a diagram illustrating an optical system in which a model eye is disposed on a path of reference light.
Figure 3:
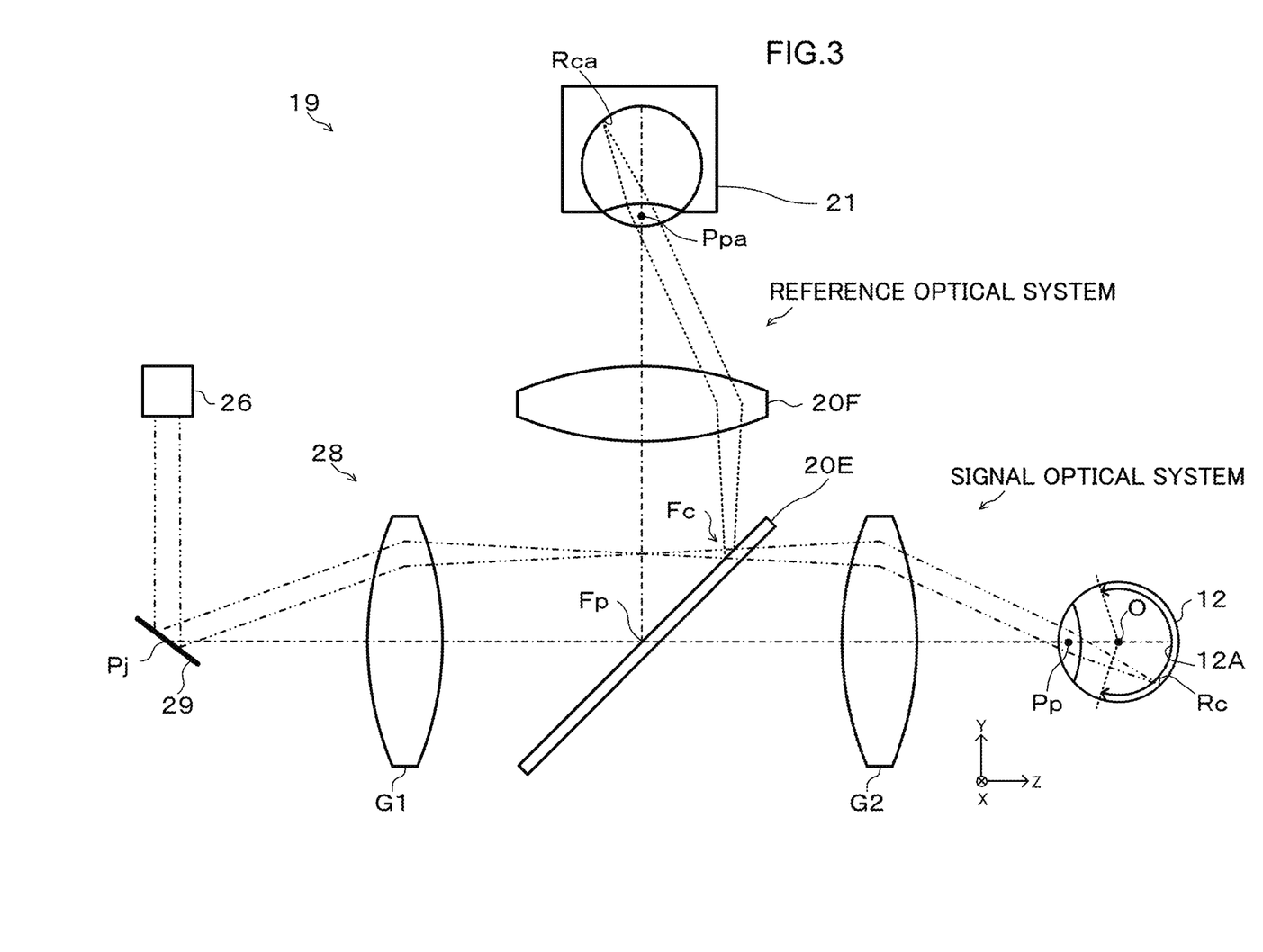
FIG. 3 is a diagram illustrating an optical system in which a model eye is disposed on a path of reference light.

Explanation next follows regarding an example of a configuration of the common optical system 28, with reference to FIG. 2 and FIG. 3.

As illustrated in FIG. 2, the common optical system 28 includes a first optical unit G1, a second optical unit G2, an optical unit 20F, the half mirror 20E, and the model eye 21. Equivalent optical systems are employed for the second optical unit G2 and the optical unit 20F such that a reference optical system and a signal optical system are optically equivalent to each other following splitting by the half mirror 20E. Note that although the first optical unit G1, the second optical unit G2, and the optical unit 20F are illustrated in side-face end view as if each were configured by a single lens, the respective optical units may each be configured by a plural lens group.

Explanation next follows regarding the manner in which OCT light passes through the common optical system 28 during OCT imaging.

FIG. 2 illustrates light paths of OCT light when the OCT light from the combining element 26 is scanned by the scanning element 29 with the angle θ in FIG. 1 set to zero.

The OCT light passes through the first optical unit G1 to reach a position Fp on the half mirror 20E. The OCT light is split into the signal light and the reference light by the half mirror 20E.

The signal light is guided by the second optical unit G2 to the pupil position Pp of the examined eye 12. A position Pj of the scanning element 29 and the pupil position Pp are in a conjugate relationship to each other. The signal light guided to the pupil position Pp is converged on a fundus Rp in the imageable region 12A. The signal light that has been reflected or scattered by the retina and the choroid at the fundus Rp then reaches the position Fp on the half mirror 20E via the second optical unit G2.

On the other hand, the reference light that was split by the half mirror 20E is guided to a pupil position Ppa of the model eye 21 by the optical unit 20F. The position Pj of the scanning element 29 and the pupil position Ppa of the model eye 21 are in a conjugate relationship to each other. The reference light guided to the pupil position Ppa is converged on a fundus Rpa of the model retina 218 (see FIG. 4) formed at a posterior eye portion surface of the model eye 21. The reflected or scattered reference light from the model retina 218 reaches the position Fp of the half mirror 20E via the optical unit 20F, and interferes with the signal light so as to generate interference light. This interference light passes the first optical unit G1, the scanning element 29, and the combining element 26, before returning to the fiber coupler 20C of the OCT unit 20 and being guided to the sensor 20B. The half mirror 20E is an example of a splitting element of the technology disclosed herein.

During SLO imaging, a non-illustrated light blocking mechanism (light blocking plate or the like) is inserted between the half mirror 20E and the optical unit 20F. The SLO light is blocked from reaching the model eye 21 by the non-illustrated light blocking mechanism, and of the SLO light, only reflected light from the examined eye 12 reaches the detection element 18B of the SLO unit 18. During SLO imaging, there is accordingly no influence on the reflected light from the examined eye 12 caused by reflected light from the model eye 21.

FIG. 3 illustrates light paths of OCT light when the OCT light from the combining element 26 is scanned by the scanning element 29 with the angle θ in FIG. 1 set to a prescribed angle. Namely, FIG. 3 illustrates light paths of OCT light when performing OCT imaging of a region peripheral to a center optical axis in a scanning operation at a prescribed angle with respect to the center optical axes of the light paths of OCT light when the angle θ is set to zero as illustrated in FIG. 2.

The OCT light passes through the first optical unit G1 to reach a position Fc on the half mirror 20E. The OCT light is split into the signal light and the reference light by the half mirror 20E.

The signal light is guided by the second optical unit G2 to the pupil position Pp of the examined eye 12 at the angle θ. The signal light guided to the pupil position Pp is converged on a fundus Rc in the imageable region 12A. The signal light reflected or scattered by the retina and the choroid at the fundus Rc then reaches the position Fc on the half mirror 20E via the second optical unit G2.

On the other hand, the reference light that was split by the half mirror 20E is guided to the pupil position Ppa of the model eye 21 by the optical unit 20F. The reference light guided to the pupil position Ppa is converged on a fundus Rca at a peripheral region of the fundus Rpa of the model retina 218 formed on the posterior eye portion surface of the model eye 21. The reference light reflected or scattered by the model retina 218 reaches the position Fc on the half mirror 20E via the optical unit 20F, and interferes with the signal light so as to generate interference light. This interference light passes the first optical unit G1, the scanning element 29, and the combining element 26, before returning to the fiber coupler 20C of the OCT unit 20 and being guided to the sensor 20B. The photoreception signal of the sensor 20B is processed by the control device 16 to generate tomographic images and 3D OCT data of the fundus.

Figure 4:
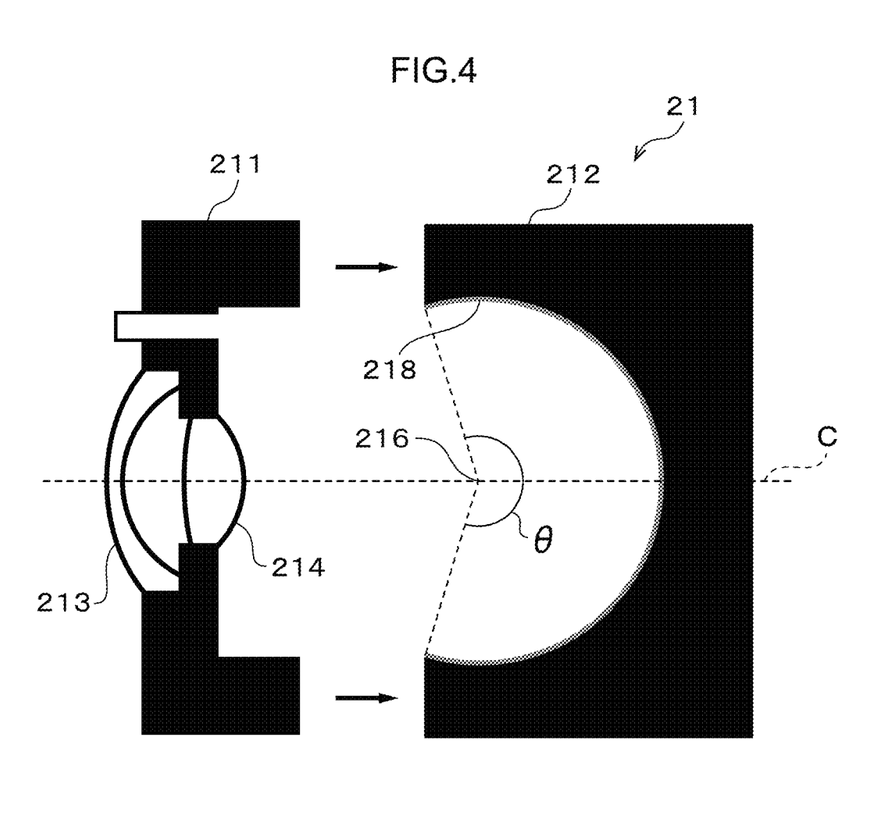
FIG. 4 is a diagram illustrating a configuration of a model eye.

Next, explanation follows regarding an example of the model eye 21 disposed on the reference light path, with reference to FIG. 4. As described below, the model eye 21 is configured so as to have optical characteristics and size similar to those of a human eye.

As illustrated in FIG. 4, the model eye 21 of technology disclosed herein includes an anterior eye portion case 211 and a posterior eye portion case 212. The anterior eye portion case 211 and the posterior eye portion case 212 are, for example, configured from a metal such as aluminum. A model cornea 213 corresponding to the cornea of a human eye, and a model lens 214 corresponding to the lens of a human eye, are incorporated into the anterior eye portion case 211.

The posterior eye portion case 212 is formed with a concave face. The radius of the concave face is set so as to be equivalent to that of the human eye (about 12 mm). A field of view θ centered on a model eye center 216 is formed with a range of 230°. The model retina 218 is formed over the entire concave face. The model eye 21 accordingly includes a concave shaped model retina formed on the concave face.

As an example of the model retina 218 of the model eye, a single layer adjusted such that the reflectance and scattering rate of the model retina 218 are equivalent to those of a retina may be formed. As another example, the case surface may be polished as appropriate so as to adjust the reflectance and scattering rate. In addition, a light absorbing coating may be applied as an undercoat to the model retina 218 in order to remove any influence caused by light reflected from the concave face of the posterior eye portion case 212.

Alternatively, the model retina 218 may be a simple mirror face, or face applied with an inorganic material film or an organic material film adjusted for light reflectance or scattering rate. Furthermore, a configuration may be adopted in which a surface on the model lens side of the posterior eye portion case 212 is a face polished so as to adjust light reflectance and scattering rate.

Figure 5:
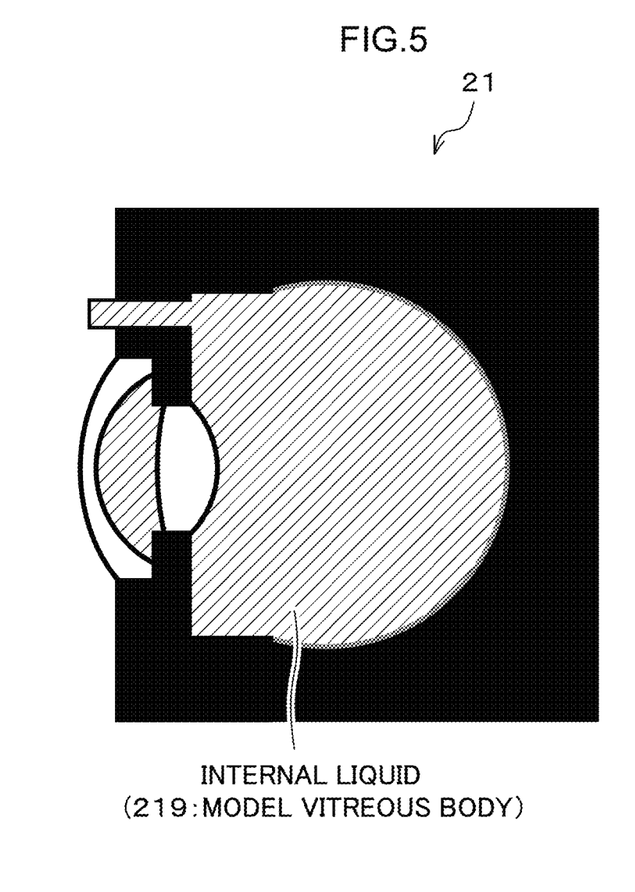
FIG. 5 is a diagram illustrating a configuration in a case in which a liquid has been injected into a model eye.

Out of the model cornea 213 and model lens 214, or the posterior eye portion case 212, at least one may be appropriately modified in shape to allow for accommodate myopia or farsightedness. Preferably, as illustrated in FIG. 5, the model eye 21 is formed by filling the interior of the anterior eye portion case 211 and the posterior eye portion case 212 with a liquid and then bonding the cases together. With regard to the liquid filling the interior, an internal liquid having a refractive index similar to that of the vitreous body of a human eye is preferably filled to configure a model vitreous body 219.

It is sufficient for the model retina 218 to be formed over a range (imageable field of view angle) corresponding to that of the imageable region 12A, and there is no limitation to cases in which the model retina 218 is formed over a field of view θ range of 230°. Depending on the actual imageable region, the range of the model retina 218 may be any out of greater than 60° greater than 80°, greater than 120°, greater than 200°, greater than 220°, or greater than 230°.

The model eye 21 is an example of a model eye of the technology disclosed herein. The model cornea 213 is an example of a model cornea of the technology disclosed herein, the model lens 214 is an example of a model lens of the technology disclosed herein, the model retina 218 is an example of a model retina of the technology disclosed herein, and the model vitreous body 219 is an example of a model vitreous body of the technology disclosed herein.

According to the first exemplary embodiment, when light from the light source 20A is being scanned by the scanning element 29 during OCT imaging, the incident angle of the signal light with respect to the pupil position Pp always matches the incident angle of the reference light with respect to the pupil position Ppa. Due to the optical unit 20F and the second optical unit G2 also being optically equivalent to each other, and the model eye 21 having substantially the same characteristics and structure as a human eye, a light path length of the reference light through the half mirror 20E, the optical unit 20F, and the model eye 21, reflected and scattered by the model retina 218, and returning to the half mirror 20E (a light path length through the half mirror 20E, the optical unit 20F, and the model eye 21, reflected and scattered by the model retina 218, and returning to the half mirror 20E), and the light path length of the signal light (a light path length through the half mirror 20E, the second optical unit G2, the examined eye 12, reflected and scattered by the retina and the choroid, and returning to the half mirror 20E), are equal path lengths, irrespective of the scanning angle.

This accordingly enables a difference in light path length between the reference light and the signal light to be prevented from getting larger as the incident angle θ of the signal light increases with respect to the center of the pupil of the examined eye 12. Namely, the intensity of interference light can be prevented from dropping in cases in which OCT imaging is performed for a region of the fundus, such as a fundus peripheral region, where the incident angle θ is large.

Moreover, the optical elements up to the half mirror 20E, i.e. the fiber coupler 20C and the first optical unit G1, are common to both the signal light and the reference light, and the optical unit 20F and the second optical unit G2 are optically equivalent units, as stated above. The wavelength distribution and the state of polarization of the reference light and the signal light accordingly match each other without the need for any particular correction and adjustment.

This means that there is no need in the ophthalmic device 110 to employ a device or configuration to make the state of polarization and wavelength distribution of the reference light and the signal light match each other in order to perform good OCT imaging. This enables the structure of the ophthalmic device 110 to be simplified.

Second Exemplary Embodiment

Next, explanation follows regarding a second exemplary embodiment. Note that the second exemplary embodiment has a similar configuration to that of the first exemplary embodiment, and so the same reference numerals will be appended to similar portions and detailed explanation thereof will be omitted.

Figure 6:
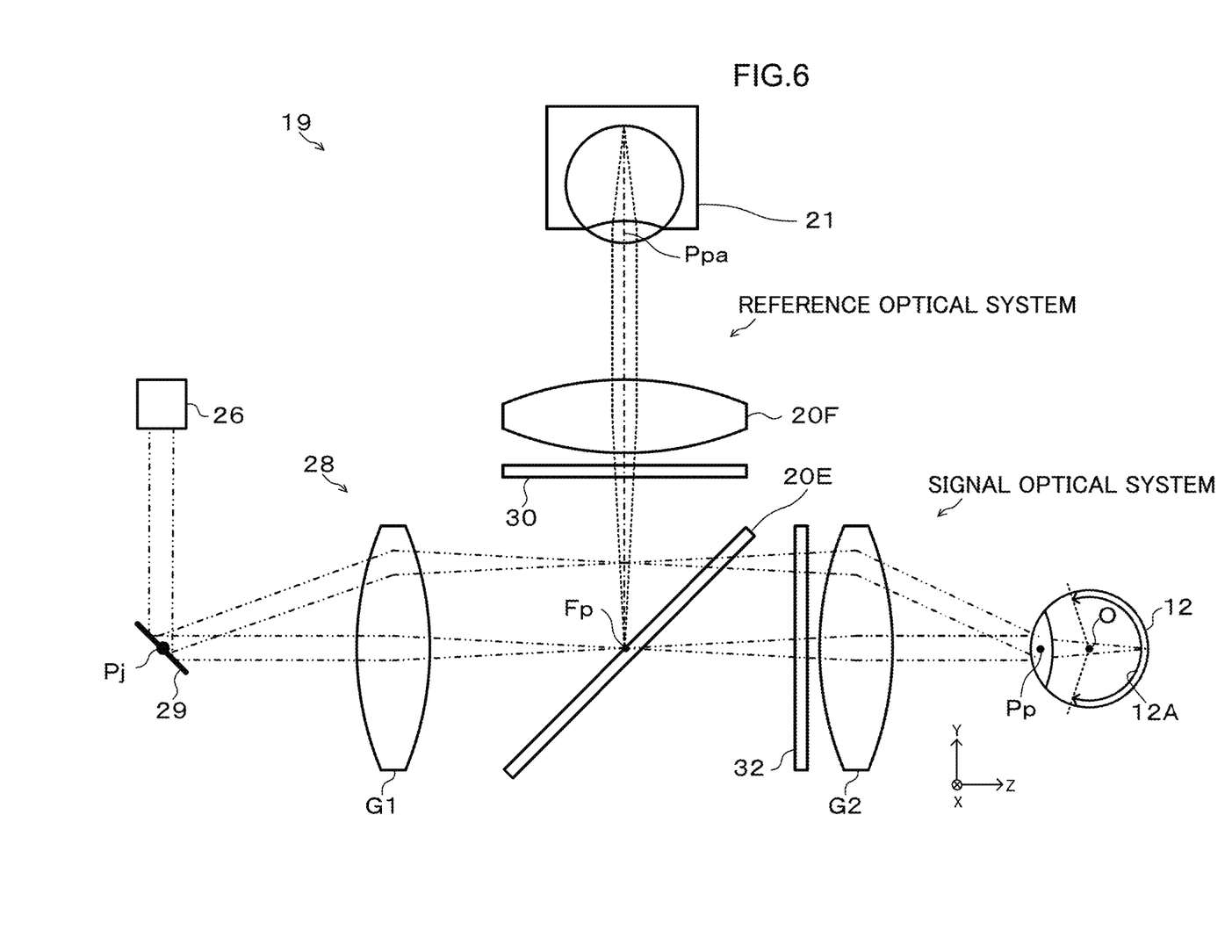
FIG. 6 is a diagram illustrating an optical system in which an optical filter is disposed on a light path.

Explanation follows regarding an example of a configuration in which the properties of the light are made to match each other in the signal light and the reference light, with reference to FIG. 6.

The configuration of the scanning optical system 19 illustrated in FIG. 6 is a configuration in which a first optical filter 30 of a reference optical system, and a second optical filter 32 of the signal optical system are inserted into the configuration of the scanning optical system 19 illustrated in FIG. 2.

More specifically, the first optical filter 30 is installed between the half mirror 20E and the optical unit 20F. The first optical filter 30 is an optical filter capable of adjusting the light intensity of reference light in order to obtain a good OCT image. An example of the first optical filter 30 is a neutral density (ND) filter. The second optical filter 32 is installed between the half mirror 20E and the second optical unit G2. The second optical filter 32 is a filter for adjusting the light path length and the wavelength distribution as changed by the first optical filter 30 inserted into the reference optical system. An example of the second optical filter 32 is a plate shaped glass material having the same thickness as the first optical filter 30. The first optical filter 30 and the second optical filter 32 are examples of light intensity adjustment element of the technology disclosed herein.

Note that the second optical filter 32 may be omitted in cases in which any change to the light path length as a result of insertion of the first optical filter 30 into the reference light path is within a predetermined tolerance range for light path length.

Moreover, in cases in which the light intensity of the reference light is low compared to the light intensity of the signal light, the first optical filter 30 and the second optical filter 32 may be swapped over.

Furthermore, the light intensities of the reference light and the signal light may be respectively adjusted by the first optical filter 30 and the second optical filter 32.

In the technology disclosed herein as described above, the properties of the light in the signal light and the reference light are made to match each other by inserting the first optical filter 30 and the second optical filter 32, thus improving the image quality of the tomographic images, or the image quality of images based on the 3D OCT data. Namely, being able to use the first optical filter 30 and the second optical filter 32 to finely adjust properties of the light in the signal light and the reference light, such as the relative light intensities and differences in the light paths, enables good OCT data and fundus tomographic images to be obtained.

First Modified Example

A case has been described above in which the reference light is formed by splitting light after the signal light has been scanned such that the light path length, the wavelength distribution, and the state of polarization are common to both the signal light and the reference light. However, the technology disclosed herein is not limited to such a configuration, and a configuration may be considered in which the model eye 21 is disposed in a reference optical system configured by an ordinary Michelson interferometer employing a fiber coupler.

Second Modified Example

Figure 7:
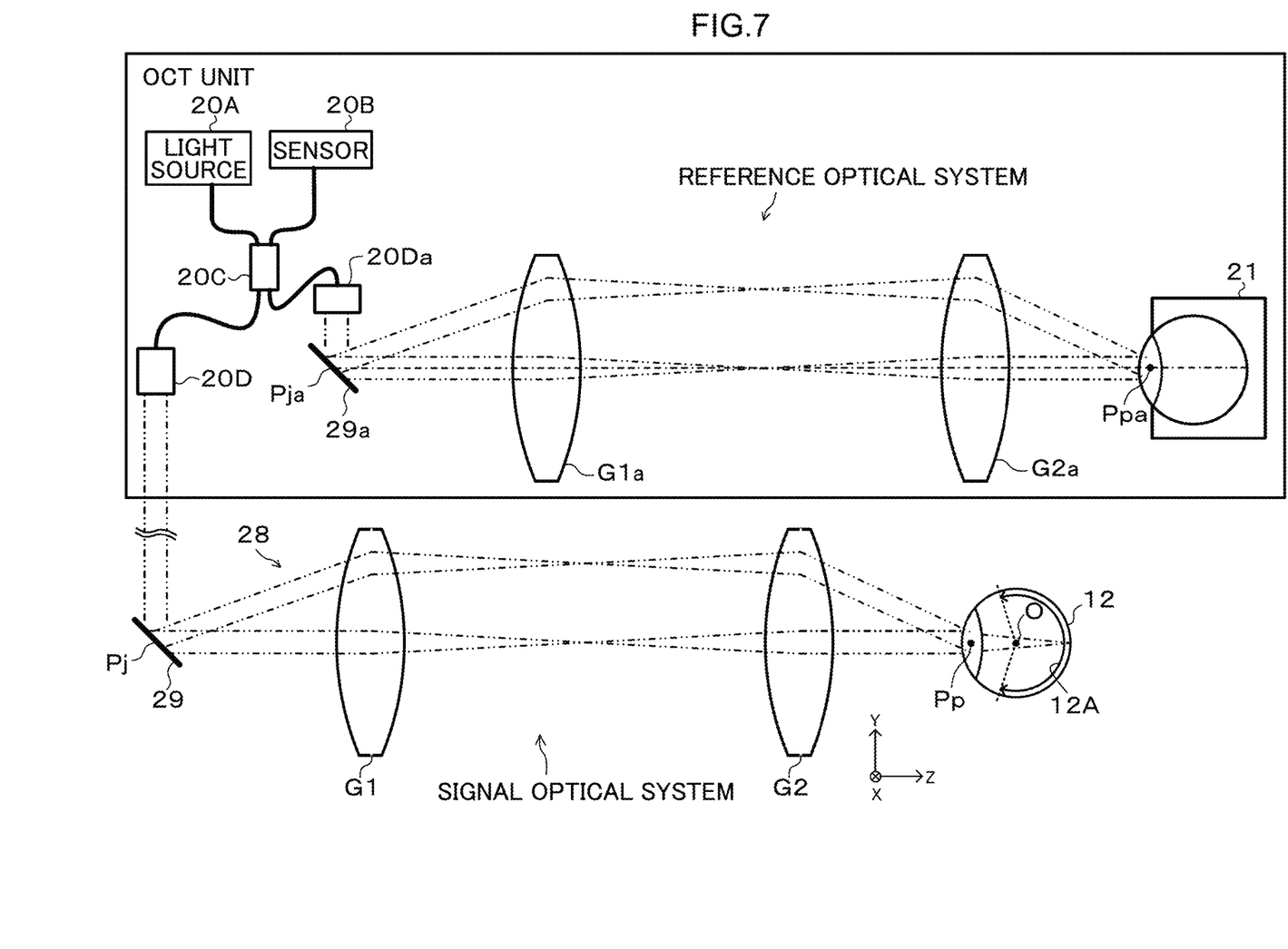
FIG. 7 is a configuration diagram illustrating an OCT optical system of a second modified example.

Explanation follows regarding a second modified example, with reference to FIG. 7.

As illustrated in FIG. 7, in the second modified example a reference optical system is formed on a light path of light that has been split by the fiber coupler 20C. More specifically, the light from the light source 20A of the OCT unit 20 passes through the fiber coupler 20C, is collimated into a parallel beam by a collimator 20D, and is emitted toward the scanning optical system 19. The signal light is scanned by the scanning optical system 19 so as to pass through the pupil of the examined eye 12 and, and signal light reflected or scattered by the retina and the choroid passes through the fiber coupler 20C so as to be incident to the sensor 20B.

On the other hand, of the light from the light source 20A, the light split by the fiber coupler 20C is collimated into a parallel light beam by a collimator 20Da, and emitted toward the model eye 21 after passing a scanner (scanning element) 29a and optical units G1a and G2a similarly to in the reference optical system described above. The reference light reflected or scattered at the model retina 218 of the model eye 21 passes through the fiber coupler 20C so as to be incident to the sensor 20B. The fiber coupler 20C is an example of a splitting element of the technology disclosed herein.

The scanning element 29 of the signal optical system and the scanner (scanning element) 29a described above of the reference optical system are driven in synchronization with each other.

Adopting such a configuration causes the different light paths of the signal light and the reference light to match irrespective of the scanning angle, in contrast to a configuration in which a simple flat mirror is disposed in the reference optical system. This accordingly enables a large light path difference to be prevented from arising between the reference light and the signal light. Namely, the intensity of interference light can be prevented from dropping in cases in which OCT imaging is performed for a region of the fundus, such as a fundus peripheral region, where the incident angle θ is large.

EXPLANATION OF THE REFERENCE NUMERALS

20 OCT unit
20C fiber coupler
20E half mirror
21 model eye
first optical filter
32 second optical filter
110 ophthalmic device
214 model lens
218 model retina
219 model vitreous body

The invention claimed is:
1. An ophthalmic device comprising:
a splitting element that splits light from a light source into a signal light and a reference light;
a model eye disposed on a reference light path of the reference light and configured to reflect or scatter the reference light at a model retina formed on a concave face;
a concave mirror configured at the model retina formed on the concave face;
an interference optical system configured to obtain interference light from the reference light that has been reflected on the concave mirror and the signal light that has been illuminated onto an examined eye and returned from the examined eye; and a scanning element that is installed on a light path of a light between the light source and the splitting element and at a position conjugate with a pupil position of the examined eye, and that, by scanning of the light, scans the signal light onto the examined eye and scans the reference light onto the concave mirror.

2. The ophthalmic device of claim 1, wherein the model eye further comprises a model lens and a model vitreous body.

3. The ophthalmic device of claim 2, wherein the model eye is installed such that a pupil position of the model eye formed by the model lens is positioned at a conjugate position to a pupil of the examined eye.

4. The ophthalmic device of claim 1, wherein the model retina has a surface coated with an inorganic material film adjusted for light reflectance or scattering rate or an organic material film adjusted for light reflectance or scattering rate.

5. The ophthalmic device of claim 1, wherein the model eye is disposed at a terminal end of the reference light path.

6. The ophthalmic device of claim 1, further comprising a light intensity adjustment element that is disposed on at least one light path of a signal light path of the signal light or the reference light path, and that is configured to adjust a light intensity of the signal light or a light intensity of the reference light.

7. The ophthalmic device of claim 1, wherein the model retina on the concave face is formed corresponding to an imageable region on the examined eye.

8. The ophthalmic device of claim 1, wherein the model retina on the concave face is formed over a range larger than 200° with respect to a center of the model eye.

9. The ophthalmic device of claim 1, further comprising:
a reference optical system that is provided at the reference light path between the splitting element and the model eye, and that guides the reference light to the model eye; and
a signal optical system that is provided at a signal light path of the signal light between the splitting element and the examined eye, and that guides the signal light to the examined eye,
wherein the reference optical system and the signal optical system are optically equivalent configurations.

10. The ophthalmic device of claim 9, wherein each of the reference optical system and the signal optical system comprises a respective optical filter.

\* \* \* \* \*